United States Patent
Sutherland et al.

(10) Patent No.: US 10,998,093 B2
(45) Date of Patent: May 4, 2021

(54) MONITOR FOR A MEDICAMENT INHALER

(71) Applicant: ADHERIUM (NZ) LIMITED, Auckland (NZ)

(72) Inventors: Garth Campbell Sutherland, Auckland (NZ); Michael James Gormack, Auckland (NZ); Darren James Bainbridge, Auckland (NZ)

(73) Assignee: ADHERIUM (NZ) LIMITED, Auckland (NZ)

( * ) Notice: Subject to any disclaimer, the term of this patent is extended or adjusted under 35 U.S.C. 154(b) by 602 days.

(21) Appl. No.: 15/533,650

(22) PCT Filed: Jan. 6, 2016

(86) PCT No.: PCT/NZ2016/050001
§ 371 (c)(1),
(2) Date: Jun. 6, 2017

(87) PCT Pub. No.: WO2016/111633
PCT Pub. Date: Jul. 14, 2016

(65) Prior Publication Data
US 2017/0325734 A1    Nov. 16, 2017

(30) Foreign Application Priority Data

Jan. 9, 2015   (NZ) .................... 703739
Feb. 2, 2015   (NZ) .................... 704348
Aug. 13, 2015  (NZ) .................... 711045

(51) Int. Cl.
*G16H 20/13*    (2018.01)
*A61M 15/00*    (2006.01)
(Continued)

(52) U.S. Cl.
CPC .......... *G16H 20/13* (2018.01); *A61B 5/4833* (2013.01); *A61M 15/00* (2013.01);
(Continued)

(58) Field of Classification Search
CPC .............. A61M 15/00; A61M 15/0003; A61M 15/0021–0026; A61M 15/0028;
(Continued)

(56) References Cited

U.S. PATENT DOCUMENTS 5,363,842 A    11/1994   Mishelevich et al.
6,958,691 B1   10/2005   Anderson et al.
(Continued)

FOREIGN PATENT DOCUMENTS

WO    9507723 A1     3/1995
WO    2013043063 A1  3/2013
(Continued)

OTHER PUBLICATIONS

International Search Report and Written Opinion issued in PCT/NZ2016/050001 dated Apr. 21, 2016.

*Primary Examiner* — Kendra D Carter
*Assistant Examiner* — Elliot S Ruddie
(74) *Attorney, Agent, or Firm* — Kenealy Vaidya LLP

(57) ABSTRACT

Adherence monitors are disclosed, incorporating cap removal sensors together with a determined time period in order to determine that a dose of medicament has been dispensed. In another form, cap removal data is combined with acoustic data to determine that a dose of medicament has been dispensed. Several specific structural arrangements are also disclosed.

14 Claims, 16 Drawing Sheets

(51) Int. Cl.
  *A61M 16/00* (2006.01)
  *A61B 5/00* (2006.01)
(52) U.S. Cl.
  CPC ........ *A61M 15/008* (2014.02); *A61M 15/009* (2013.01); *A61M 15/0026* (2014.02); *A61M 15/0035* (2014.02); *A61M 15/0041* (2014.02); *A61M 15/0043* (2014.02); *A61M 15/0051* (2014.02); *A61M 15/0091* (2013.01); *A61M 16/0003* (2014.02); *A61B 5/0002* (2013.01); *A61M 15/0003* (2014.02); *A61M 15/0023* (2014.02); *A61M 15/0028* (2013.01); *A61M 15/0071* (2014.02); *A61M 2016/0021* (2013.01); *A61M 2202/064* (2013.01); *A61M 2205/14* (2013.01); *A61M 2205/18* (2013.01); *A61M 2205/215* (2013.01); *A61M 2205/332* (2013.01); *A61M 2205/3306* (2013.01); *A61M 2205/3368* (2013.01); *A61M 2205/3375* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/8206* (2013.01); *A61M 2205/8275* (2013.01); *A61M 2205/8293* (2013.01)
(58) Field of Classification Search
  CPC .......... A61M 15/0035; A61M 15/0041; A61M 15/0043; A61M 15/0051; A61M 15/0068–0083; A61M 15/009; A61M 15/0091; A61M 16/0003; A61M 2016/0021; A61M 2202/064; A61M 2205/14; A61M 2205/18; A61M 2205/215; A61M 2205/3306; A61M 2205/332; A61M 2205/3368; A61M 2205/3375; A61M 2205/3553; A61M 2205/3584; A61M 2205/3592; A61M 2205/502; A61M 2205/50–52; A61M 2205/8206; A61M 2205/8275; A61M 2205/8293; A61B 5/0002; A61B 5/4833; G06F 19/3456; G06F 19/00

See application file for complete search history.

(56) References Cited

U.S. PATENT DOCUMENTS

| | | |
|---|---|---|
| 8,161,968 B2 | 4/2012 | Augustyn et al. |
| 8,342,172 B2 | 1/2013 | Levy et al. |
| 8,424,517 B2 | 4/2013 | Sutherland et al. |
| 8,464,707 B2 | 6/2013 | Jongejan et al. |
| 8,746,242 B2 | 6/2014 | Connell et al. |
| 2013/0008436 A1* | 1/2013 | Von Hollen ...... A61M 15/0086 128/200.14 |
| 2014/0000598 A1 | 1/2014 | Sutherland et al. |
| 2014/0182584 A1 | 7/2014 | Sutherland et al. |
| 2016/0051776 A1* | 2/2016 | Von Hollen ...... A61M 16/0003 128/200.23 |
| 2016/0325057 A1* | 11/2016 | Morrison .......... A61M 15/0091 |
| 2016/0325058 A1* | 11/2016 | Samson ................ G16H 40/67 |
| 2016/0354557 A1* | 12/2016 | McPherson Allnutt ..................... A61M 16/04 |

FOREIGN PATENT DOCUMENTS

| | | |
|---|---|---|
| WO | 2014004437 A1 | 1/2014 |
| WO | 2014147550 A1 | 9/2014 |
| WO | 2014204511 A2 | 12/2014 |
| WO | 2015030610 A2 | 3/2015 |

\* cited by examiner

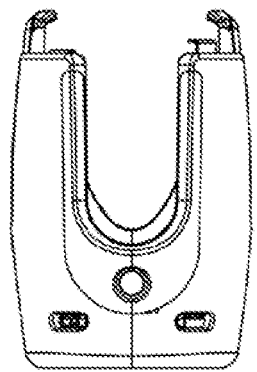
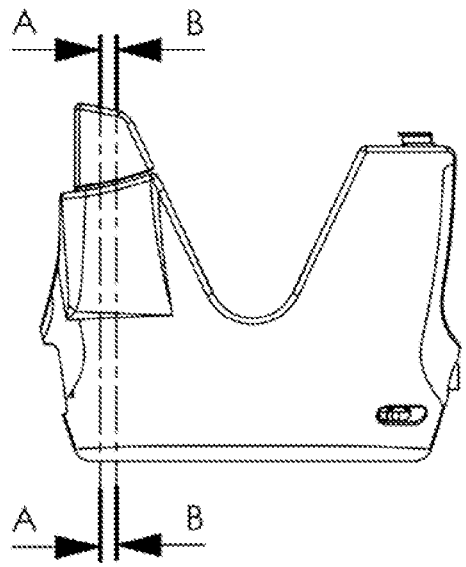
FIG. 9A
FIG. 9B
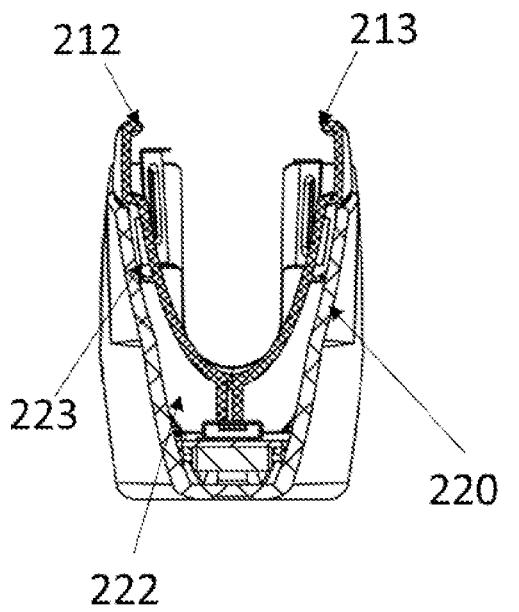
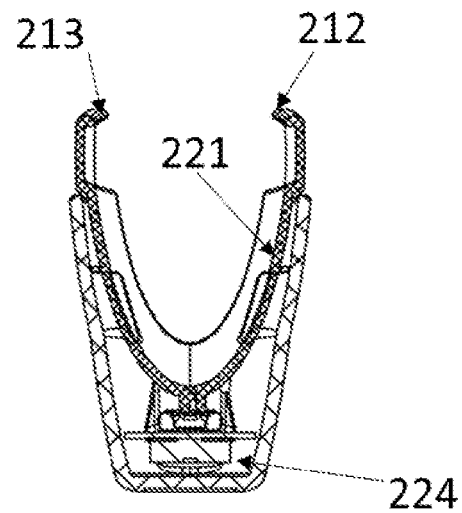
FIG. 9C
FIG. 9D

317

315

MONITOR FOR A MEDICAMENT INHALER

TECHNICAL FIELD

The present invention relates to methods, devices and systems for monitoring adherence to medication regimes which use inhalers.

BACKGROUND OF THE INVENTION

The invention is concerned with adherence monitors for inhalers with a mouthpiece cap or cover. These are often used in the treatment of respiratory diseases such as asthma, COPD, cystic fibrosis, and bronchiectasis. However, such devices may also be used to deliver other medications, for example for the treatment of pain, heart conditions, erectile dysfunction, diabetes, and other indications. The general term cap or cover will be used interchangeably to refer to all such covers and caps, however constructed, which serve to close or protect the mouthpiece when it is not is use, and are opened or removed when the inhaler is to be used.

A common type of medicament inhaler is what is known as a pressurised metered dose inhaler (pMDI). Such inhalers generally comprise a medicament canister and an actuator. The medicament canister contains medicament under pressure and is designed to deliver a metered dose of medicament in the form of an aerosol spray. The actuator comprises a generally L-shaped hollow tube which has a first open end adapted to receive the medicament canister, and a second open end which acts as a mouthpiece. The mouthpiece is usually fitted with a removable cap.

Another type of medicament inhaler is a dry powder inhaler (DPI). A common type of dry powder inhaler is in the form of a generally tube-shaped body (e.g. a TURBU-HALER® which is manufactured and marketed by Astra-Zeneca AB), which includes an internal store of a suitable medicament; a rotatable base for dispensing a single dose of the medicament into an appropriate inhalation chamber; and a mouthpiece, through which a user may inhale the medicament that has been dispensed into the inhalation chamber. Such dry powder inhalers usually come with a removable and replaceable screw-cap, adapted to cover the mouthpiece and tube-shaped body of the inhaler, when the inhaler is not in use.

Another common type of a DPI is in the form of a disc (e.g. GSK's Diskus® inhaler) which includes a priming lever, and the priming lever, when actuated, dispenses a metered dose of medicament in the form of a dry powder into an appropriate receptacle adjacent a mouthpiece (which is usually covered by a cap when the DPI is not being used). The dry powder may then be inhaled by the user (namely, by sucking strongly on the mouthpiece of the inhaler).

Another type of medicament inhaler is a breath-actuated inhaler (BAI). A BAI is in the form of a pMDI or a DPI in which the dose is delivered by a triggering mechanism internal to the inhaler in response to inspiratory flow rates exceeding certain pre-set levels, i.e. a patient's inhalation causes the dose to be delivered. An example of such a pMDI BAI is the Easi-Breathe® which is manufactured and marketed by Ivax/Teva.

Another type of DPI is an inhaler in which the medicament is held within a capsule which is perforated by the user (e.g. by a use of a piercing button on the inhaler) prior to the inhalation during which the medicament is delivered (e.g., HandiHaler® manufactured and marketed by Boehringer Ingelheim Pharma GmbH & Co. KG). Other types of DPI are also known (e.g. Genuair® by Almirall).

Another type of DPI inhaler is ELLIPTA® (manufactured and marketed by GSK), and sold under a number of brand names: ANORO®ELLIPTA®, BREO®ELLIPTA®, INCRUSE®ELLIPTA®, RELVAR®ELLIPTA®. The ELLIPTA® DPI is described in a number of granted patents and patent applications, e.g., U.S. Pat. Nos. 8,161,968 and 8,746,242.

A problem associated with the use of all medicament inhalers is poor adherence. Many studies have shown that users frequently do not take their medicament at the predetermined or prescribed times and/or in the required amounts. The consequences of this non-adherence can include reduced disease control, lower quality of life, lost productivity, hospitalisation and avoidable deaths. This represents a considerable cost to the users, as well as to the health system.

To address this problem, there are now available a number of adherence monitoring devices for use with medicament inhalers. The adherence monitors include dose detection means and means for transmitting the adherence data gathered, either wirelessly or otherwise, to a device such as, for example, a docking station, website, cloud computing network or a smartphone, tablet or personal computer (belonging to the user or a health professional). This adherence data may be transmitted in real time or at predetermined set times. Examples of patents which describe such technology are U.S. Pat. No. 6,958,691 (Anderson et al.), U.S. Pat. No. 8,424,517 (Sutherland et al.) and U.S. Pat. No. 8,342,172 (Levy et al.), U.S. Pat. No. 5,363,842 (Mishelevich et al.), U.S. Pat. No. 8,464,707 (Jongejan et al.), WO 95/07723 (Wolf et al.), US Patent Application No. 2014/0000598 (Sutherland), WO 2013/043063 (Sutherland) and WO 2015/030610 (Sutherland).

WO 2014/147550 (von Hollen et al.) discloses a system configured to monitor the usage of a respiratory medicament delivery device, the system comprising a means for selectively connecting and disconnecting the power supply from a processor by means of respectively, removing or replacing a tethered cover from/onto the mouthpiece of the pMDI. The von Hollen device utilises the cap on/off motion only for the purposes of connecting/disconnecting power supply to the processor. The cap on/off is not detected per se. The dose detection means is separate from the cap on/off motion and instead relies on the use of other sensors.

There are also available adherence monitoring devices which detect the on/off position of the cap fitted onto the mouthpiece of a pMDI.

PCT/NZ2014/000184 (Sutherland et al.) describes an adherence monitoring device with cap detection means, which detects cap removal/replacement in relation to the mouthpiece of a medicament inhaler. A separate dose detection means is provided. The cap detection is not used to detect if a dose is dispensed.

Adherence monitors known in the art use cap removal detection in conjunction with other sensors to detect actuation and/or inhalation.

It is a general object of the present invention to provide a monitoring device for a medicament inhaler, in which dose detection is both cost effective and sufficiently accurate.

It is a further object of specific aspects of the present invention to provide a monitoring compliance system for a medicament inhaler which is suitable for use with, for example, the HandiHaler® and the Ellipta® inhaler, and similar devices.

SUMMARY OF THE INVENTION

In a first broad form the present invention, provides a monitor which detects that a medicament has been dispensed using a combination of only acoustic data and cap removal data.

In another broad form, the present invention provides a monitor which detects that a medicament has been dispensed using cap removal data and a time window indicative of medicament being dispensed.

According to one aspect the present invention provides a monitor for an inhaler, the inhaler including a medicament dispenser and a cap, the monitor including an acoustic sensor, a cap removal sensor, and a processor including analysis software, wherein the processor operatively receives acoustic sensor data from the acoustic sensor and cap removal data from the cap removal sensor, the processor determining that a dose of medicament has been dispensed only if the cap removal sensor data indicates that the cap has been removed, and the acoustic sensor data indicates that a later acoustic signal consistent with the dispensing of medicament has occurred.

According to another aspect the present invention provides a monitor for an inhaler, the inhaler including a medicament dispenser and a cap, the monitor including cap removal sensor, and a processor including analysis software, wherein the processor operatively receives cap removal data and cap replacement data from the cap removal sensor, the processor determining that a dose of medicament has been dispensed only if the cap removal sensor data indicates that the cap has been removed and replaced, and wherein a predetermined minimum time between cap removal and cap replacement is detected.

According to a further aspect the present invention provides monitor for an inhaler, the inhaler including a medicament dispenser and a cap, the monitor including a flexible inner shell adapted to receive the inhaler in an interference fit, and an outer shell, such that the inner shell is adapted to flex to receive the inhaler relative to the outer shell.

According to a further aspect, the present invention provides monitor for an inhaler, the inhaler including a medicament dispenser and a cover, the cover opening by pivoting at a pivot point relative to the body of the inhaler, the monitor including at least one cover open and closed sensor, located adjacent the cover.

According to a further aspect, the present invention provides a method for detecting that a dose of medicament has been dispensed by an inhaler, the inhaler including a medicament dispenser and a cap, including at least the steps of: receiving cap removal sensor data indicating that the cap has been removed, and cap replacement data indicating that the cap has been replaced; receiving acoustic sensor data; processing the cap removal data and cap replacement data to determine a cap removed time period; processing the acoustic sensor data to determine whether a predetermined acoustic signature is detected; wherein a dose of medicament is determined to be dispensed only if said time period is within predetermined limits, and if said acoustic signature is detected.

According to a further aspect, the present invention provides a method for detecting that a dose of medicament has been dispensed by an inhaler, the inhaler including a medicament dispenser and a cap, including at least the steps of: receiving cap removal sensor data indicating that the cap has been removed, and cap replacement data indicating that the cap has been replaced; processing the cap removal data and cap replacement data to determine a cap removed time period; wherein a dose of medicament is determined to be dispensed only if said time period is within predetermined limits.

According to a further aspect, the present invention provides method for detecting that a dose of medicament has been dispensed by an inhaler, the inhaler including a medicament dispenser and a cap, including at least the steps of: receiving cap removal sensor data indicating that the cap has been removed, and cap replacement data indicating that the cap has been replaced; receiving acoustic sensor data; processing the cap removal data and cap replacement data to determine that the cap had been removed and replaced; processing the acoustic sensor data to determine whether a predetermined acoustic signature is detected; wherein a dose of medicament is determined to be dispensed only if said cap has been removed and replaced, and if said acoustic signature is detected.

The present invention according to some embodiments provides two novel adherence monitors suitable for use with HandiHaler® inhaler and Ellipta® inhaler. The releasably attachable adherence monitors described in prior art are designed for use with pMDIs, grind-type DPIs, disc-shaped inhaler devices. To date no releasably attachable monitors have been developed that are suitable for use with an Ellipta® inhaler. This may be due to the particular design and functional features, which pose a number of attachment/dose detection challenges. For example, to ensure proper priming of the inhaler and successful dose delivery, the full range of mouthpiece cover motions must be uninterrupted. The vent and the dose counter must be unobstructed and the adherence monitor must not interfere with the inhaler's flat base design.

BRIEF DESCRIPTION OF THE DRAWINGS

An illustrative embodiment of the present invention will be described with reference to the accompanying figures, in which:

FIG. 9A is a side view of the adherence monitor illustrated in FIGS. 5-8;

FIG. 9B is a front view of the embodiment illustrated in FIG. 9A with vertical lines indicating the line of cross-section and arrows A and B indicating two cross-sectional views shown in detail in FIGS. 9C and 9D below;

FIG. 9C is a cross-sectional view of the adherence monitor illustrated in FIGS. 9A and 9B; with the view direction as indicated by the arrows A in FIG. 9B;

FIG. 9D is a cross-sectional view of the adherence monitor illustrated in FIGS. 9A and 9B; with the view direction as indicated by the arrows B in FIG. 9B;

DETAILED DESCRIPTION OF THE INVENTION

Figure 1:
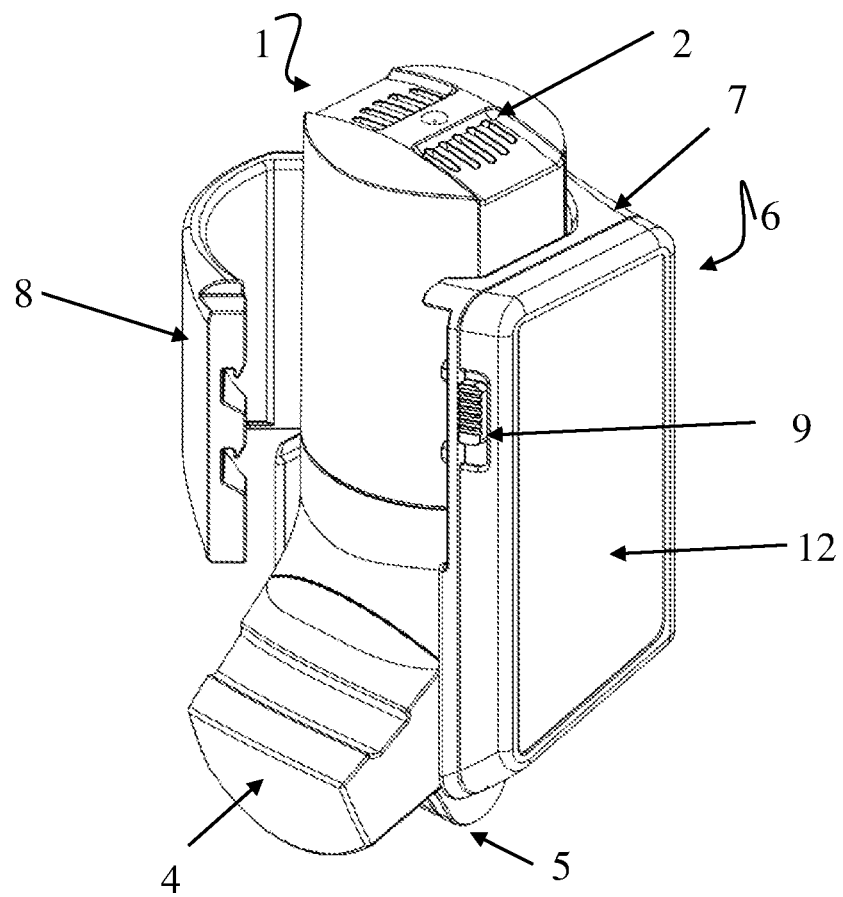
FIG. 1 is a perspective view of the first embodiment of the invention, with the medicament inhaler (Easi-Breathe® by Teva Group/Ivax) installed and the hinged door of the adherence monitor open.

Throughout this specification, the terms "patient" or "user" or "person" or "patient usage", when used in relation to the use of a medicament delivery device, are to be understood to refer to any person that uses a medicament delivery device.

The present invention will be described in relation to various specific implementations, which it will be understood are intended to be illustrative and not limitative of the scope of the present invention. It will be appreciated in particular that various additional features and functions, indicators and the like may be included in monitors which implement the present invention. These may be selected for specific application at the option of the product designer.

The following implementations will be described with reference primarily to dry powder inhalers (DPIs), breath-actuated inhalers (BAIs), and pressurized metered dose inhalers (pMDIs) as these are in widespread commercial use. However, the present invention may, with suitable modifications as will be apparent to those skilled in the art, be applied to other designs of inhalers, presently known or yet to be developed. The general term inhaler will be used to refer to any such inhaler device, unless a contrary intention is apparent from the context.

Similarly, whilst the discussion below is principally in relation to respiratory related medicaments, it is applicable to any use of inhaler devices, including by way of example only pain medication, diabetes, erectile dysfunction, or other conditions. The present invention is concerned with the monitoring of how the medication is used and dispensed, and should in no way be considered as limited to any particular medicament or condition. The terms medicaments and medication should be broadly construed, and are not limited to any specific indication or types of inhalable substances.

The present invention is concerned with inhaler devices which incorporate a cover or cap. The function of the cap or cover is to prevent foreign bodies or contamination from entering the device or affecting the mouthpiece when it is not in use. In some forms the cap is removable, for example by unscrewing or removing a force fit cap. The cap is preferably tethered to the inhaler. In other forms of inhaler, the cover may be hinged, pivoting or otherwise moving to take the inhaler from an inoperative to an operative state. The general term cap will be used to refer to all such covers and caps, however constructed, which serve to close or protect the mouthpiece when it is not is use, and are opened or removed when the inhaler is to be used. Similarly, the term cap removal refers to any such operation to remove the cap or cover or otherwise ready the inhaler for use, and cap replacement refers to replacing the cap or closing the cover or otherwise placing the inhaler into its inoperative condition.

It will be appreciated that the present invention will be described with reference to implementations which are intended to be supplied as a device to be used over many replacement inhalers, attaching to one and then removing when the inhaler is no longer used, for attachment to a new inhaler. It could be sold as part of or attached to an inhaler and removed for attachment to another inhaler. However, the present invention may also be implemented as an integral part of an inhaler. It could be sold as an inhaler with an embedded adherence monitor and disposed together with the inhaler device.

As a general explanation, the implementations of an adherence monitor described are intended to be used with a medicament dispensing inhaler with a mouthpiece cover. The devices include systems to detect that a dose has been dispensed, and to retain or communicate a record of this to a remote system, for example via Bluetooth® to a smartphone, tablet or other device. The intention is to automatically create a record of usage, to assist in clinical management. The devices may also provide reminders to the user, detect whether or not a dispensing device is attached, provide error indications, or provide other functions.

Figure 2:
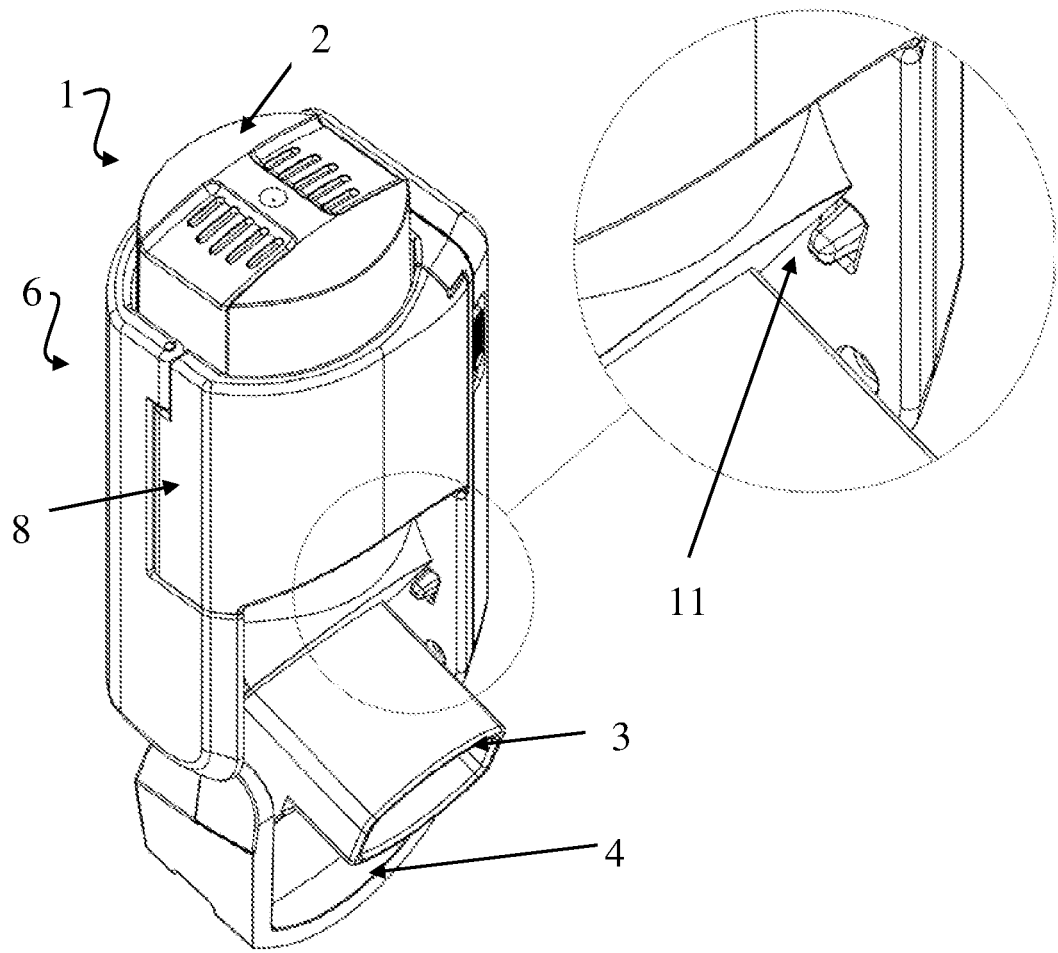
FIG. 2 is a perspective view of the embodiment illustrated in FIG. 1, with the hinged door closed, the cap removed from the mouthpiece of the medicament inhaler and an enlarged view of the cap removal switch shown.
Figure 3A:
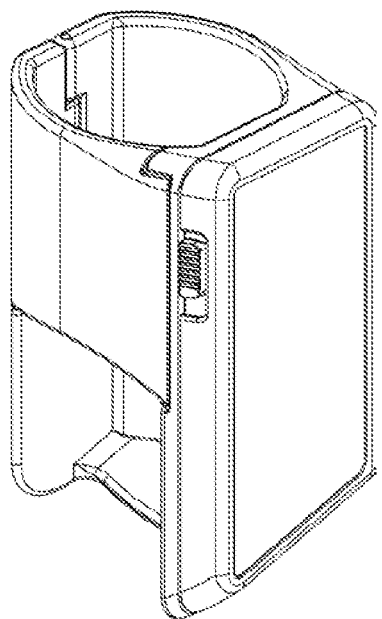
FIGS. 3A-D are perspective views of all four sides of the adherence monitor illustrated in FIGS. 1 and 2.
Figure 3B:
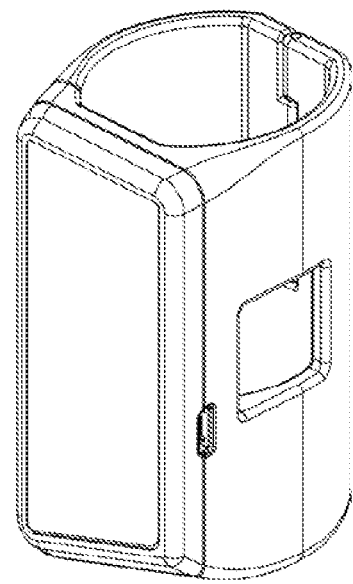
Figure 3C:
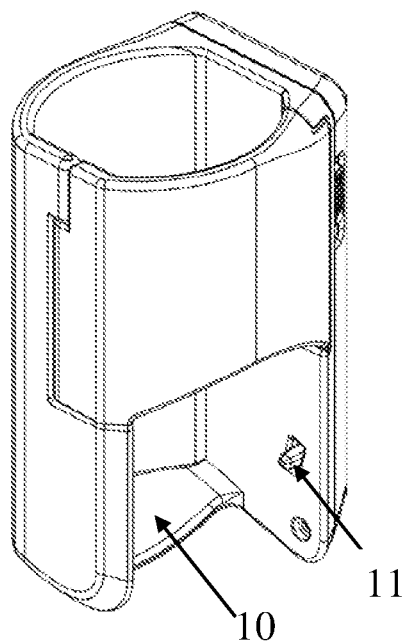
Figure 3D:
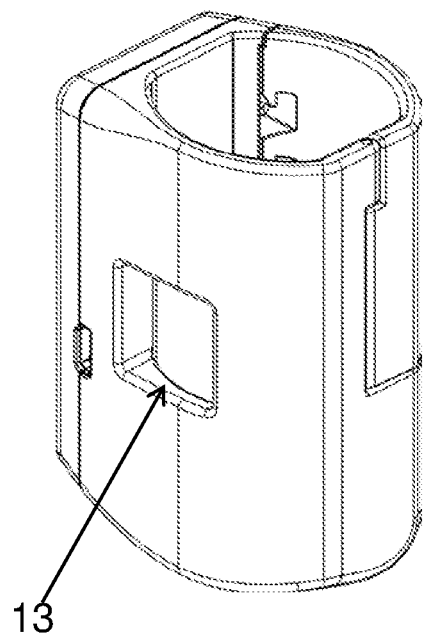

Referring to FIGS. 1 and 2 there is shown a medicament inhaler generally indicated by arrow 1. The medicament inhaler is a BAI medicament inhaler (namely, Easi-Breathe® by Teva Group/Ivax).

The medicament inhaler 1 includes a store of medicament in the form of a pressurised medicament canister (not shown), and a first housing (for housing the canister) in the form of an actuator 2.

The inhaler 1 is also provided with a medicament dispensing means for delivering a dose of medicament. The medicament dispensing means is in the form of a spray stem (not shown) extending from the canister (not shown), which is adapted to engage with a spray-directing element housed within the actuator 2. When the canister is pushed down into the actuator 2 (in the case of BAI's by a mechanical or electro-mechanical trigger mechanism or manually by the patient in case of non-BAI pMDIs), the spray stem and spray-directing element combine to deliver a metered dose of medicament out through the mouthpiece 3 of the actuator 2, and into the mouth of the user (who sucks on the mouthpiece 3).

The inhaler 1 is also provided with a removable and replaceable cap 4, which is adapted to close off the mouthpiece 3 when the inhaler 1 is not in use.

The cap 4 ensures that the mouthpiece 3 remains clean, and free from dust and grime, and also ensures that no foreign objects can enter the mouthpiece 3 (for example when the inhaler is not in use or being carried in a pocket or purse), which may otherwise present a choking hazard.

The cap 4 is releasably attached to the base of the actuator 2 by a hinge mechanism 5. Having the cap 4 hinged to the actuator 2 in such a fashion ensures that the cap 4 is not inadvertently dropped or lost once it has been removed. Other types of cap connection are also possible. In some embodiment, the cap may be releasably attachable to the medicament inhaler by the use of a tether. In another embodiment, the cap may be completely detachable from the mouthpiece of the medicament inhaler.

As well as inhaler 1, there is also an associated adherence monitor, generally indicated by arrow 6. The adherence monitor 6 is housed within a second housing 7, which is releasably attachable to the inhaler 1 (or more specifically to the actuator 2). The second housing 7 fully encloses (or fully encircles) the inhaler 1. In some embodiments the second housing 7 may attach to the inhaler 1 by friction, mechanical coupling, adhesive coupling or other releasable coupling methods.

In the example illustrated, the second housing 7 includes a hinged door 8, which when open, allows the inhaler 1 to be installed within the second housing 7. When the inhaler 1 is placed in the second housing 7, as illustrated in FIG. 2, the hinged door 8 is closed and subsequently locked, using the sliding lock mechanism 9.

The base of the inhaler 1 (or actuator 2) rests on the ledge 10 of the second housing 7, wherein the ledge 10 supports the inhaler 1 but does not interfere with the opening or closing of the cap 4 or the operation of hinge mechanism 5.

The second housing 7 contains a cap detection means in the form of a switch 11. The switch 11 is positioned on an inner wall of the second housing 7. The switch 11 is positioned so that when the cap 4 is placed on the mouthpiece 3, the cap 4 actuates the switch 11. The switch 11 is configured to be open when the cap 4 is removed from the mouthpiece 3, and closed when cap 4 is replaced onto mouthpiece 3.

The switch may be mechanical, electromechanical or electronic. In another embodiment, the switch may be optical, whereby a beam of light (e.g., IR light) may detect the presence of the cap when it is on the mouthpiece and the absence of the cap when the cap is removed from the mouthpiece. Of course, the open/closed states indicated could be reversed.

Preferably, the switch 11 is a surface mount detector switch combined with a mechanical lever. The arrangement and construction may be such that the cap actuates the switch when the cap is on the mouthpiece and deactivates the switch when the cap is off (or removed from) the mouthpiece, or vice versa.

The adherence monitor 6 is adapted, through its hardware, firmware and/or software, to monitor and/or manipulate and/or store and/or transmit adherence data relating to patient usage of the inhaler 1.

The adherence monitor 6 includes an ECM (not shown) which is included within the side 12 of the second housing 7. The ECM is configured to process and/or cause storage and/or transmission of adherence data relating to patient usage of the inhaler 1. The ECM is also configured to process data relating to cap 4 removal/replacement from/onto the mouthpiece 3. The action of removing and/or replacing the cap 4 results in an actuation (or deactuation) of the switch 11 (by the cap 4) and an appropriate electrical signal is sent to the ECM.

Preferably, no additional dose detection sensors are included in the adherence monitor and the dose detection log is instead processed by the ECM based on the data received from the switch 11 and data recorded in the memory. The ECM is able to determine cap-off events which are likely to constitute a medicament dose delivery event, from other cap-off events.

The ECM may be configured to cause the information relating to the cap-on/cap-off events to be recorded in the memory. The information may include inhaler-in log, type of inhaler, time stamp for the cap on/cap-off event. Preferably, the ECM may be configured to analyse cap-on/cap-off events to determine that a medicament dose delivery event has or has not occurred.

Preferably, the ECM may be able to determine the likelihood of a medicament dose delivery event occurring based on the amount of time that the cap is removed from (or off) the mouthpiece, before being replaced onto the mouthpiece.

Testing by the inventors has shown that it is unlikely that a person could remove the cap from the mouthpiece, deliver a dose of medicament, and subsequently replace the cap, in less than three seconds. Accordingly, the ECM may determine that a dose of medicament is likely to have been dispensed if the cap is removed from the mouthpiece for longer than three seconds, before being replaced.

Hence, if a person inadvertently dislodges the cap from the mouthpiece, and immediately replaces the cap, in (for example) less than three seconds, then the ECM will in this implementation determine that a medicament dose delivery event has not occurred.

The ECM may also be adapted to determine that a medicament dose delivery event has not occurred if the cap is removed from the cap for longer than a predetermined length of time, for example 10 seconds or 20 seconds. Such occurrences may, for example, be due to the cap being inadvertently dislodged without the knowledge of the person who carries the inhaler, for example the cap may become dislodged in a handbag or pocket belonging to the person.

Preferably, the ECM may be configured to cause a medicament dose delivery event to be stored in the memory. The ECM may also be configured to receive and store in the memory outputs from any other sensors connected to the ECM.

As well as the ECM being capable of processing data relating to cap removal/replacement from/onto the mouthpiece, the ECM may also be adapted to monitor and/or manipulate and/or store and/or transmit any type of sensor or adherence data relating to patient usage of the medicament inhaler via the communication means. Such ECM's will be familiar to those skilled in the art of adherence monitoring technology for medicament inhalers. The ECM may also determine and/or store other related data, for example time information, location, communications connection status, operation data relating to the monitor, and data as known in the art.

Figure 4:
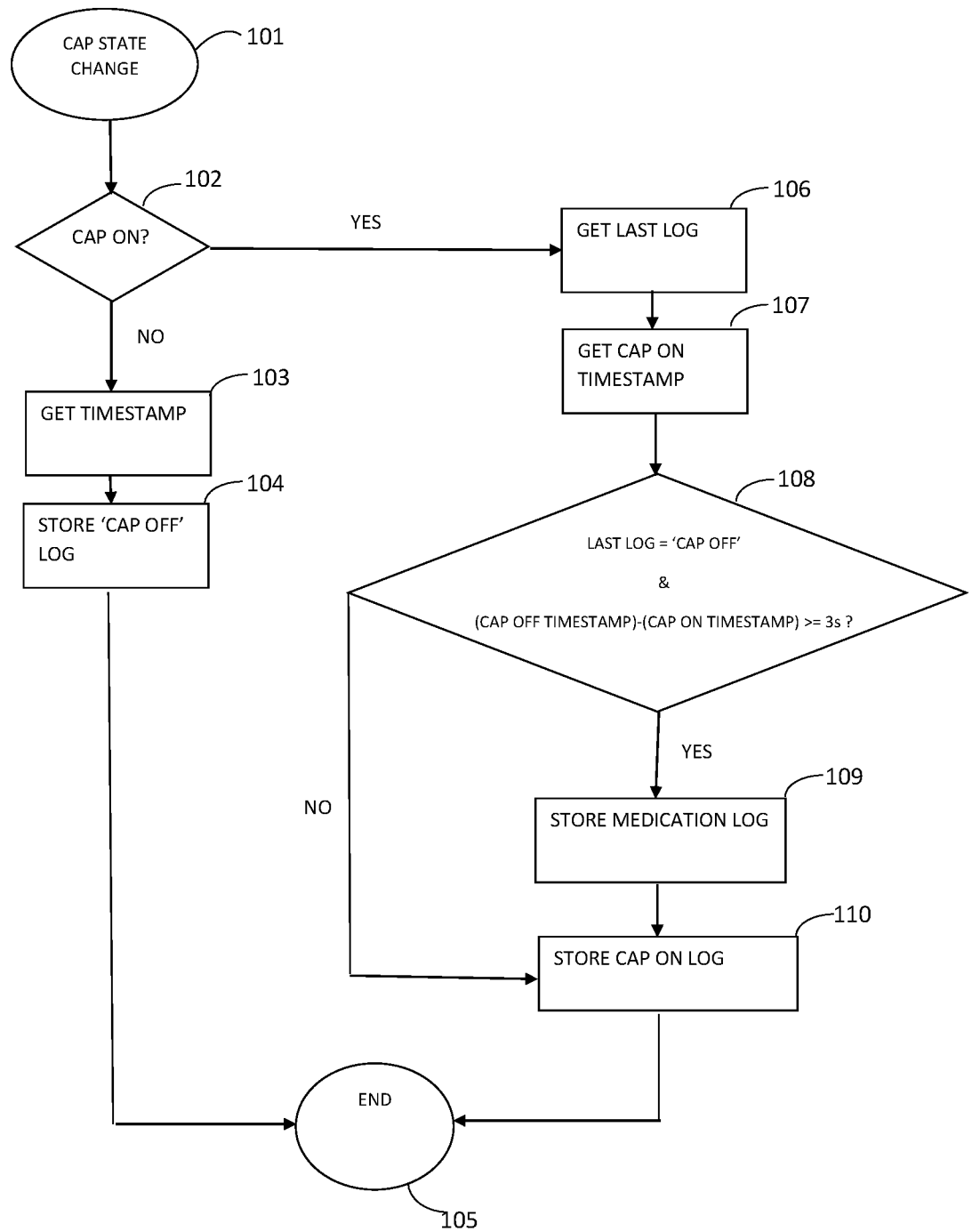
FIG. 4 is a flow chart representing a method for detecting a cap removal ("cap of") event likely to constitute a medicament dose delivery event.

FIG. 4 show a method for determining whether a cap-off event is likely to constitute a medicament dose delivery event, and allowing for a medicament dose delivery to be distinguished from other cap-off events.

First, the ECM detects "inhaler in" (that is, when the inhaler 1 is placed within the adherence monitor 6) utilising the input from any known sensors (e.g. optical sensor, pressure sensor) (step not shown).

Once the presence of the inhaler is detected by the ECM, any change of the switch 11 status (i.e. cap state change) may be detected at step 101. Following the cap change state signal 101, the ECM determines if the cap 4 is on at step 102. If the cap 4 is off the mouthpiece 3, the ECM generates a time stamp for the 'cap off' event at step 103 and causes a 'CAP OFF' log to be stored at step 104. This completes the first part of the method at step 105.

A subsequent change in the switch 11 state is detected by ECM at step 101. The ECM again determines if the cap 4 is on the mouthpiece 3 of the inhaler 1 (at step 102). If the cap 4 is on the mouthpiece 3, the ECM retrieves the last cap event log stored at step 106 (i.e. the last 'CAP OFF' log stored). Subsequently, the ECM generates a time stamp for the 'CAP ON' event at step 107.

In the following step 108, the ECM analyses if the difference between the last 'CAP OFF' and current 'CAP ON' time stamps. If the 'CAP OFF' log is followed by a 'CAP ON' and the cap 4 has been off (open) for 3 seconds or more before the 'CAP ON' log, the ECM causes a medication log to be stored at step 109 and a 'CAP ON' log to be stored at step 110. If the time lapse between the last 'CAP OFF' and the 'CAP ON' logs is shorter than 3 seconds, the ECM logs the 'CAP ON' event at step 110, but no medication log is stored and the second part of the method is completed at step 105.

The ECM may be additionally configured to enter no medication log if the difference between 'CAP OFF' and 'CAP ON' logs exceeds a certain predetermined length of time. For example, if the cap 4 is removed from the mouthpiece 3 for longer than 10 seconds or 20 seconds the ECM may log no medication event or an error cap event.

The adherence monitor 6 also includes a battery and memory (not shown) both included within the side 12 of the second housing 7.

In another aspect of the present invention, the adherence monitor 6 may further include a communication means (not shown) located within the second housing, in communication with the ECM and memory and configured to send and/or receive data to and from remote locations and/or electronic devices external to the adherence monitor 6. The communication means may be included within the side 12 of the second housing 7. In some implementations it may be integral with the ECM.

Further, the adherence monitor 6 may include a user interface (not shown) located within the second housing 7, and being in communication with the ECM and memory and configured to enable data, cues, results and/or instructions and any other communicable items to be communicated between the user (e.g. a patient, a medical professional) and the ECM, memory or computing device external to the adherence monitor.

The user interface may be included within/on the side 12 of the second housing 7. Because the second housing 7 is releasably attachable to the inhaler 1, it may be appreciated that the adherence monitor 6 may be portable and/or reusable across a range of different medicament inhalers.

For inhalers with internal dose counter displays, the second housing 7 may include a dose counter window 13, to allow the user easy access/viewing of the doses remaining in the device.

The adherence monitor may also include any other features which are also commonly associated with known adherence monitors. For example, the adherence monitor may include a power management system (such as a battery—rechargeable or otherwise), a memory and a communication means, in connection with the ECM.

In one embodiment, the adherence monitor may include indication means to alert the user if the ECM determines a predetermined condition. For example, the indication means may be activated if the cap is removed from the mouthpiece for longer than 10 or 20 seconds. Alternatively, the indication means may be activated if the ECM determines that a medicament dose delivery event has occurred.

The second housing may preferably be releasably attachable to the medicament inhaler. In such an embodiment, the adherence monitor may be portable and/or reusable across a range of different medicament inhalers. The second housing may be adapted to partially enclose the medicament inhaler (and/or the first housing associated with same). Alternatively, the second housing may be adapted to fully enclose and/or encircle the medicament inhaler (and/or the first housing associated with same).

Figure 5:
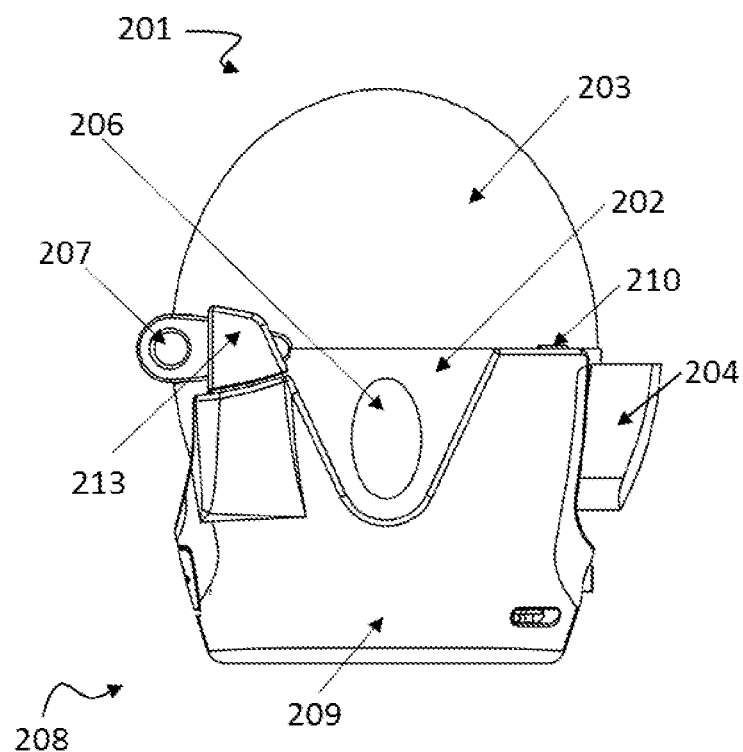
FIG. 5 is a front view of another possible embodiment of the invention, with the medicament inhaler (HandiHaler® by Boehringer Ingelheim Pharma GmbH & Co. KG) installed and the cap of the medicament inhaler closed.
Figure 6:
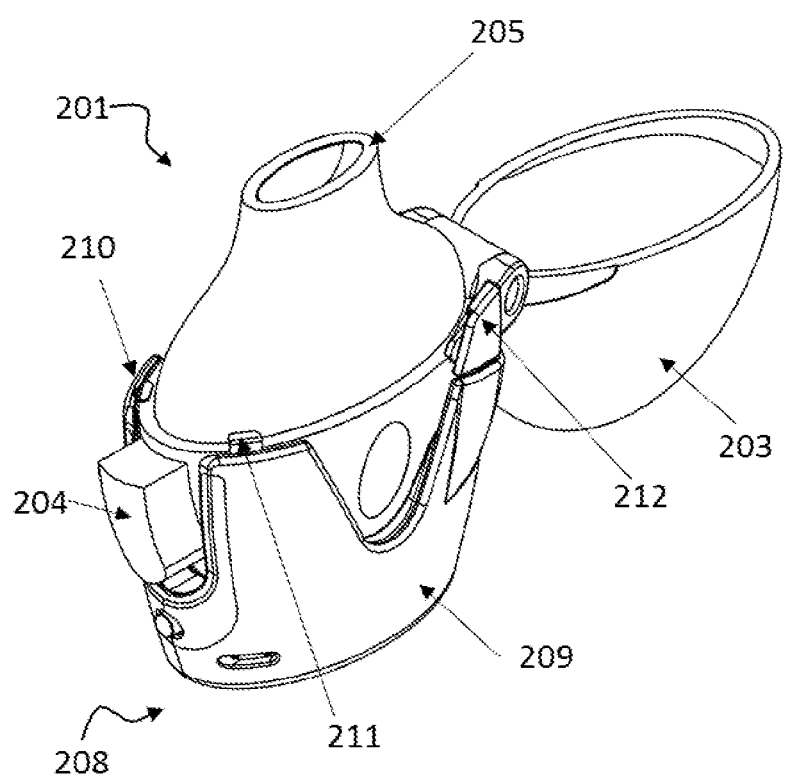
FIG. 6 is a perspective view of the embodiment illustrated in FIG. 5, with the cap removed from the mouthpiece of the medicament inhaler.
Figure 7:
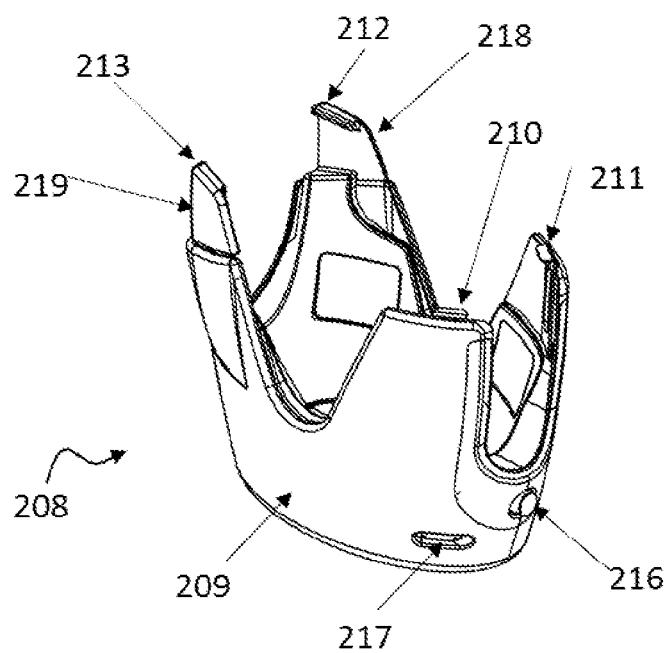
FIG. 7 is a perspective view of the front of the adherence monitor illustrated in FIGS. 5 and 6.
Figure 8:
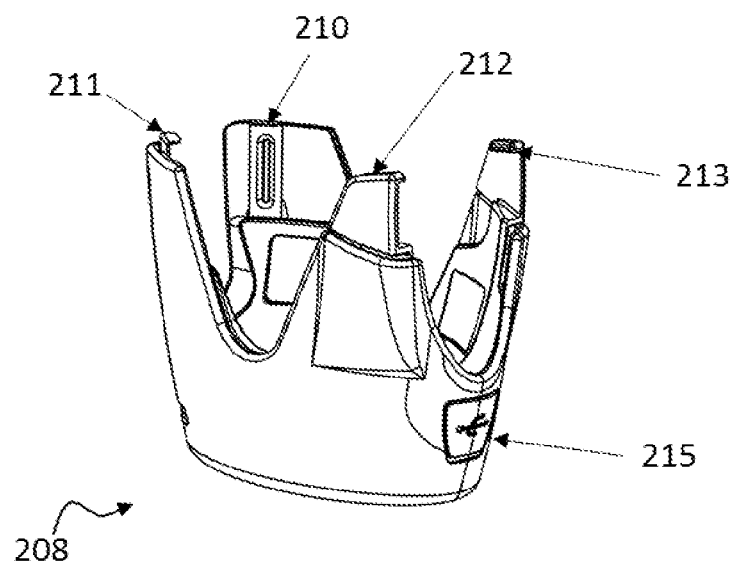
FIG. 8 is a perspective view of the rear of the adherence monitor illustrated in FIGS. 5 to 7.

Having regard to FIGS. 5 and 6 there is shown a medicament inhaler generally indicated by arrow 201. The medicament inhaler is a DPI BAI medicament inhaler (namely, a HandiHaler® by Boehringer Ingelheim Pharma GmbH & Co. KG).

The medicament inhaler 201 includes a first housing consisting of a base 202, cap 203, piercing button 204, mouthpiece 205 and a centre chamber (visible through window 206).

To administer a medicament from the HandiHaler®, the patient first opens the cap 203, followed by opening the mouthpiece 205 to provide access to the centre chamber. Both the cap 203 and the mouthpiece 205 are attached to the base 202 via a hinge mechanism 207. The patient inserts a capsule containing the medicament in powder form and closes the mouthpiece 205 firmly against the base 202 until a click is heard. The patient then presses the piercing button 204 which causes the perforation of the capsule within the centre chamber. Having exhaled, the patient then places the mouthpiece 205 in his/her mouth and inhales. The medication capsule should vibrate during a successful inhalation. After the dose has been dispensed, the mouthpiece 205 is opened again and the empty medication capsule is discarded.

Also illustrated in FIGS. 5 and 6 is an associated adherence monitor 208. Adherence monitor 208 is housed within a second housing 209, which is releasably attachable to the inhaler 201.

In suitable embodiments the second housing 209 may attach to the inhaler 201 by friction, mechanical coupling, adhesive coupling, magnetic coupling or other releasable coupling methods.

In other embodiments the second housing 209 may be attached to the inhaler with a pin arrangement (not shown) wherein a single pin or two short pins could be provided to insert into the hole present in the centre of the hinge mechanism 207 of the inhaler 201.

In the example of the invention illustrated in FIGS. 5 and 6, to insert the inhaler 201 into the adherence monitor 208, the user first opens the cap 203 and then slides the inhaler 201 on an angle, piercing button 204 first, into the adherence monitor 208, to the point where the top edge of the base 202 of the inhaler 201 is retained under a retaining catch 210 and a cap detecting switch 211. To complete the insertion of the inhaler 201 into the second housing 209, the outward pressure of the walls of the base 202, pushes out the retaining catches 212 and 213. The flexibility of the retaining catches 212 and 213 allows the base 202 of the inhaler 201 to fit into the second housing 209 and the sides of the hinge mechanism of the inhaler 201 to be retained by retaining catches 212 and 213. The insertion is completed when the base 202 of the inhaler 201 is securely retained in the second housing 209 by retaining catches 210, 212 and 213 and the cap detecting switch 211, while the mouthpiece 205 and the cap 203 may be freely opened and closed.

In the above example of the invention, the release of the medicament inhaler 201 from the second housing 209 may occur as follows. First the user flexes the retaining catches 212 and 213 away from the sides of the hinge mechanism 207. This allows the user to grip the sides of the hinge mechanism 207 of the inhaler 201 and slide it out on an angle, hinge mechanism 207 first, from the second housing 209.

FIGS. 7, 8, 9A-D and 10, show the adherence monitor 208 without medicament inhaler 201 inserted in it. The construction of the second housing 209 may be such that the wings 218 and 219, with respective retaining catches 212 and 213, have sufficient flexibility to allow for the insertion and removal of the base 202 but that they also securely retain the inhaler 201 within second housing 209.

In some embodiments the wings 218 and 219 may be spring-loaded or moulded out of flexible plastic. In other embodiments the wings 218 and 219 may be made of metal.

In the example of the invention illustrated in FIGS. 9A-D, the second housing 209 consists of an outer wall 220 and an inner wall 221. The assembly of the second housing 209 is such that in a portion of the second housing 209, the inner wall 221 and the outer wall 220 are separated from each other allowing for the flexing and/or the outward-inward movement of the outer wall 220 with respect to the inner wall 221. The space between the inner wall 221 and the outer wall 220 is hollow as indicated by arrow 222.

FIG. 9C shows an embodiment of the invention wherein a foam pad 223 is inserted between the inner wall 221 and the outer wall 220. The insertion of foam pad 223 is one possible method of increasing the range of the flexing and/or the outward-inward movement of the outer wall 220 with respect to the inner wall 221.

The wings 218 and 219, and the retaining clips 212 and 213 form part of the inner wall 221 and because of the gap between the outer wall 220 and the inner wall 221, the wings 218 and 219 have sufficient flexibility to allow for the easy insertion and removal of the medicament inhaler 201 from the second housing 209. Any other comparable retention projections may be used, in order to enhance the retention of the inhaler.

In another embodiment, a latch mechanism (not shown) may be used to grip the inhaler 201 within the second housing 209. In such embodiment the latch mechanism may consist of a latch trigger and grip fingers. The latch trigger may be placed at the bottom of the second housing 209. The pressure of the inhaler 201 inserted into the second housing 209 and against the latch trigger would cause the grip fingers of the latch mechanism to snap around the base 202 of the inhaler 201.

The adherence monitor 208 includes a cap detection means in the form of the cap detecting switch 211. The cap detecting switch 211 is positioned within the inner wall 221 of the second housing 209 so that when the cap 203 is placed on the mouthpiece 205 (that is, when the mouthpiece is closed), the cap 203 actuates the cap detecting switch 211. The cap detecting switch 211 may be configured to be open/closed when the cap 203 is removed from or replaced onto the mouthpiece 205. In some embodiments the cap detecting switch 211 may be metal. Preferably, the cap detecting switch 211 is spring-loaded.

The adherence monitor 208 may be adapted, through its hardware, firmware and/or software, to monitor and/or manipulate and/or store and/or transmit adherence data relating to patient usage of the inhaler 201.

Figure 10:
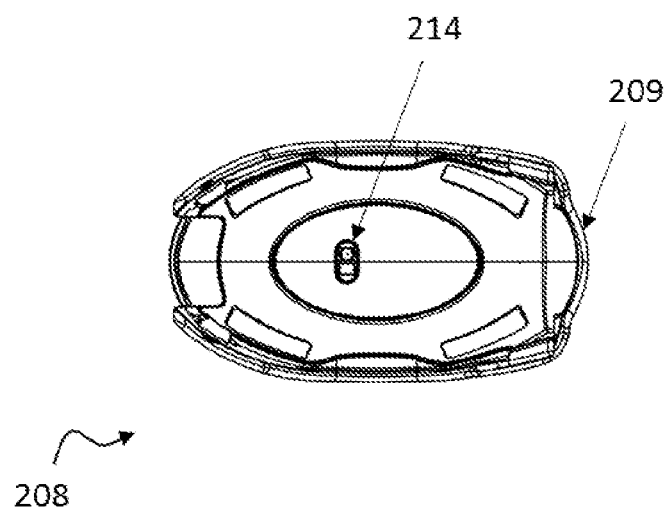
FIG. 10 is a top view of the adherence monitor illustrated in FIGS. 5-8.

As shown in FIG. 10, the adherence monitor 208 may include an optical proximity sensor 214 to detect the absence or the presence of the inhaler 201 within the second housing 209. For example, the optical proximity sensor may be an IR sensor, or any other suitable device.

Similar to the example described above in relation the adherence monitor 6, the adherence monitor 208 also contains an ECM (not shown) which is included within one of the side walls or the base of the second housing 209. As described earlier, the ECM is configured to process data relating to the removal of cap 203 from mouthpiece 205. Following each actuation or deactuation of the cap detecting switch 211 a signal is sent to the ECM.

The adherence monitor 208 may utilise the method for determining a cap-off event which is likely to constitute medicament dose delivery event and for distinguishing it from other cap-off events already described in relation to FIG. 4.

The adherence monitor 208 also includes a battery and memory (not shown), both included within one of the side walls or the base of the second housing 209. Preferably, the battery, the memory and the ECM are included within the base of the second housing 209, in the space between the inner wall 220 and the outer wall 221 of the second housing 209, for example as indicated by arrow 224 in FIG. 9D.

In another aspect of the present invention, the adherence monitor 208 may further include a communication means in communication with the ECM and memory, configured to send data to and/or receive data from remote locations and/or electronic devices external to the adherence monitor 208. In one embodiment, this may be in the form of, or provided for, by a USB port 215 located on the second housing 209.

Alternatively and/or additionally, the adherence monitor 208 may be provided with a wireless transmitter and/or a wireless transceiver to be able to transmit and/or receive data respectively, for example via Bluetooth, or any other suitable communications protocol.

Further, the adherence monitor 209 may include a user interface being in communication with the ECM and the memory and configured to enable data, cues, results and/or instructions and any other communicable items to be communicated between the user (e.g. patient, a medical professional) and the ECM, memory or computing device external to the adherence monitor 208.

In one embodiment, this may be in the form of a multi-function status button 216 and LEDs 217 for monitoring several aspects of the adherence monitor 208. For example, pushing the button 216 once may result in a green LED showing if the adherence monitor 208 is fitted to the inhaler 201 correctly, and in normal working order. Conversely, a red LED may indicate a problem. Pushing the status button 216 twice may provide for another aspect of the adherence monitor to be checked or reported, and furthermore pushing and holding the status button 216 may result in yet another function or check being done.

In some embodiments, the adherence monitor 209 described in the present invention may include a firmware for determining a cap-off event which is likely to constitute a medicament dose delivery event and distinguishing it from other cap-off events, e.g., as illustrated in FIG. 4 above.

Figure 16:
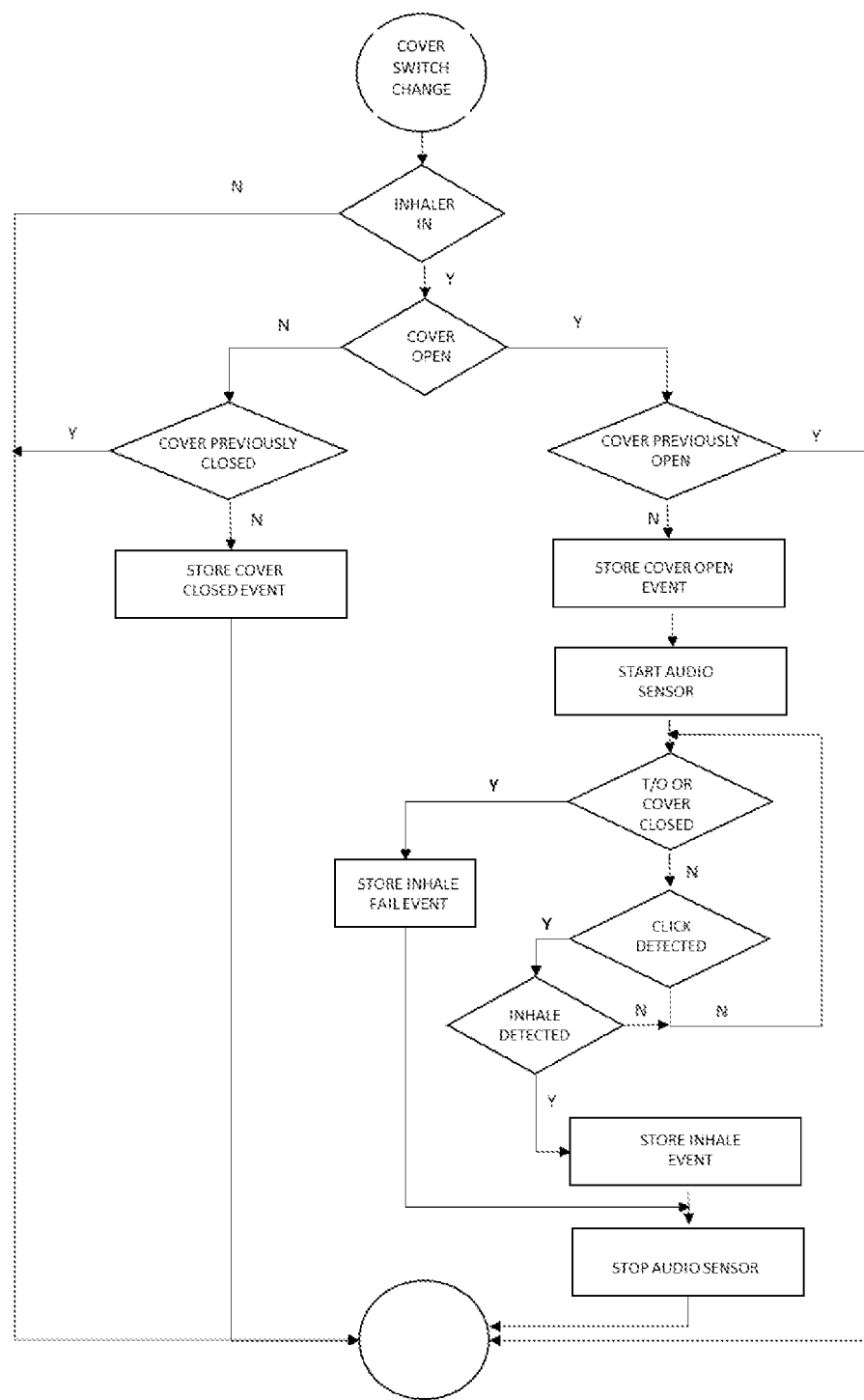
FIG. 16 is a flow chart illustrating the processing steps performed by the adherence monitor of FIGS. 11 to 15, to determine if a valid medicament inhalation has occurred.

Alternatively, the adherence monitor 209 described in the present invention may incorporate firmware for combining cap detection sensors with the acoustic dose and/or inhalation detection methods, for example the method described in relation to FIG. 16. The Ellipta® is a handheld inhaler with a built-in dose counter. Its characteristic design features include a flat base, a stand up design, an oval curve to its side walls, and a top portion and a curved mouthpiece cover. The cover for the mouthpiece is movably mounted on the inhaler allowing the user to move the cover sequentially from the first, "at rest" (or closed) position, in which the cover covers the mouthpiece, to the second, primed position, in which the mouthpiece is at least partly-uncovered, to the third, actuated (or fully open) position in which the mouthpiece is fully uncovered.

The cover for the mouthpiece is coupled with a dispensing mechanism such that movement of the cover from the primed position to the actuated position, but not from the "at rest" position to the primed position, results in actuation of the dispensing mechanism.

The movement of the cover from the "at rest" position is coupled via gearing to a strip advancement mechanism which moves two blister strips towards a central opening station where the strips are peeled and medicament from open medicament pockets is available for mixing with inhaled air and delivery into patient's airways. Once the cover is moved from the primed to the actuated position, the inhaler emits an audible click and the patient can then inhale the medication; the patient exhales away from the inhaler, then inhales through the inhaler (making sure that the vents are unobstructed), holds their breath for 3-4 seconds, exhales, and slides the cover back into the "at rest" position.

Figure 11:
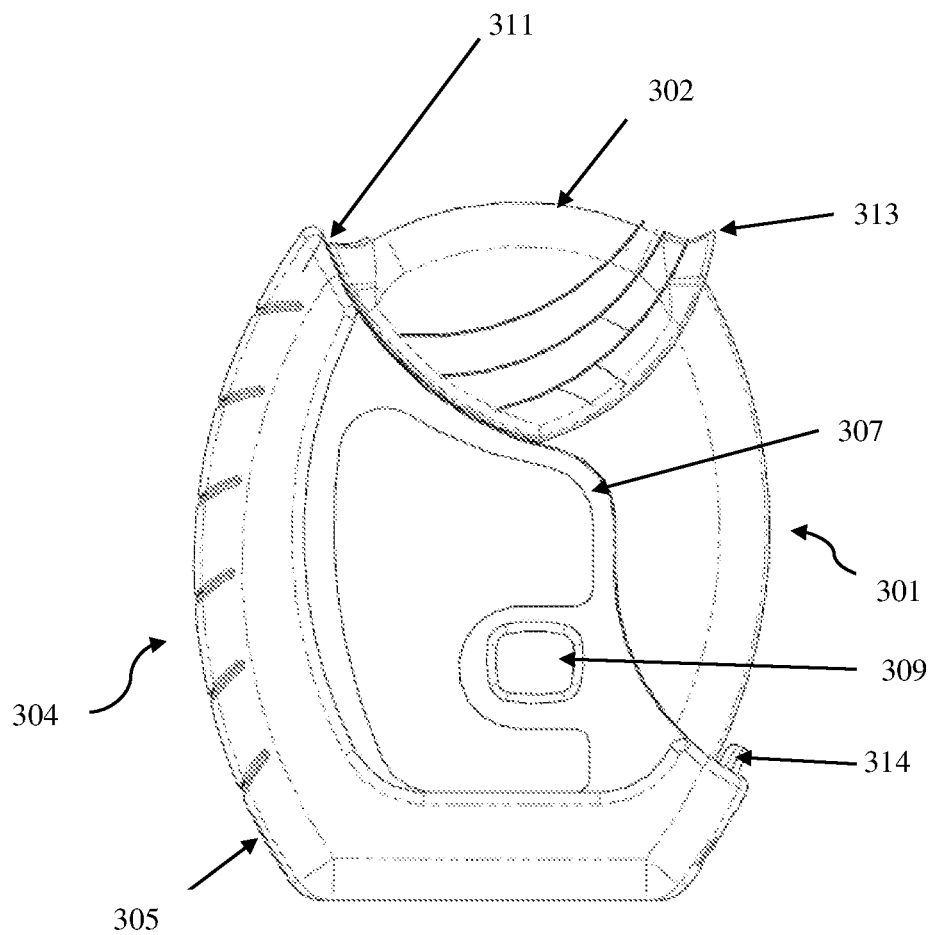
FIG. 11 is a view of an Ellipta® inhaler attached to one possible embodiment of the adherence monitor, with the inhaler cover in the "at rest" position.
Figure 12:
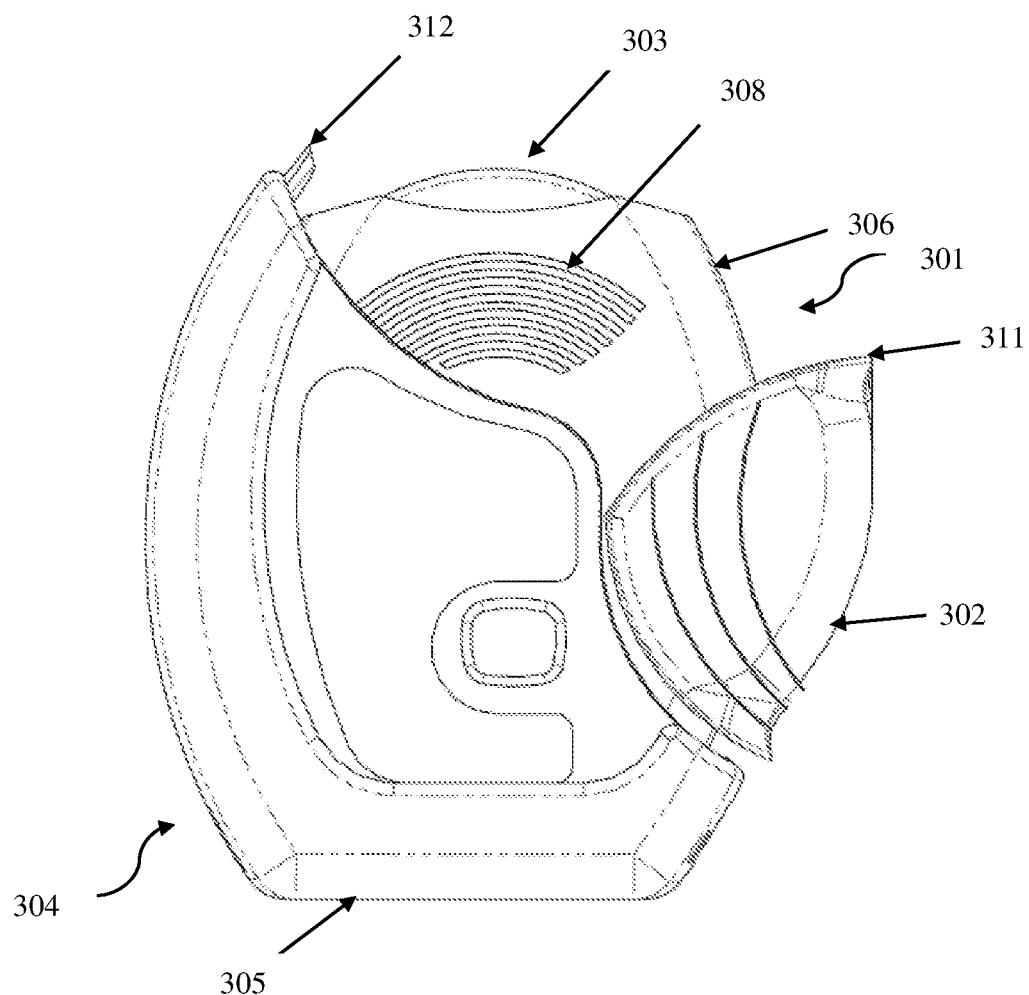
FIG. 12 is a view of an Ellipta® inhaler attached to another possible embodiment of the adherence monitor, with the inhaler cover in the actuated position.

Having regard to FIGS. 11 and 12, there is shown an inhaler generally indicated by arrow 1. The inhaler is an Ellipta® inhaler marketed by GlaxoSmithKline.

The retractable cover 302 of the inhaler 301 is coupled to a dispensing mechanism (not shown) such that movement of the cover 302 from the "at rest" position shown in FIG. 11, through an intermediate primed position (not shown) and into to the actuated position (shown in FIG. 12) actuates the dispensing mechanism.

FIG. 11 shows cover 12 in the "at rest" position, in which the cover covers the mouthpiece 303. FIG. 12 shows the cover 302 in the actuated position, in which the medication is ready for inhalation by the patient.

The inhaler 301 is attached to the adherence monitor, generally indicated by arrow 304. The housing 305 of the adherence monitor 304 is releasably attachable to the inhaler 301. In some embodiments the housing 305 may attach to the inhaler 301 by friction, mechanical coupling, adhesive coupling or other releasable coupling methods.

In the example illustrated in FIG. 11, the housing 305 attaches to the base of the inhaler 301, the full side wall opposite to the wall 306 onto which the movable cover 302 opens into the actuated position. The attachment is via an interference grip.

Preferably, the housing has sufficient proximity to the edge of the mouthpiece cover for the movement of the cover from/to the "at rest" position and to/from the actuated position to be detected by at least one cover removal sensor located on the adherence monitor housing. Preferably the adherence monitor includes a housing which is releasably attachable to the medicament inhaler.

The housing 305 further includes transparent sections 307 and 307' (307' not shown) which cover the front and back of the inhaler 301, without interfering with the movement of the cover 302, the ventilation fan 308 or the visibility of the dose counter display 309 or medication labels. The housing 305 has no contact with the cover when it is between the "at rest" and the actuated position.

The housing 305 may further attach to the portion of the wall adjacent to the mouthpiece 303 via a metal catch or finger 310 (FIG. 13), which additionally secures the adherence monitor 304 onto the inhaler 301.

When the cover 302 is in the "at rest" position, the housing 305 has sufficient proximity to the edge 311 of the cover 302 for the movement of the cover 302 from/to the "at rest" position to be detected by cover removal sensor 312 located on the adherence monitor housing 305.

The housing 305 has sufficient proximity to the edge 313 of the cover 302 for the movement of the cover 302 to/from the actuated position to be detected by cover removal sensor 314 located on the adherence monitor housing 305.

In the example illustrated, the cover removal sensors 312 and 314 are electromechanical switches. The switches are positioned so that:

(a) when the cover 302 is placed on the mouthpiece 303, the edge 311 of the cover 302 actuates the sensor 312; the sensor 312 is configured and positioned to detect an opened/closed state when the cover 302 is removed from the mouthpiece 303 or replaced onto mouthpiece 303; and (b) when the cover 302 is moved into the actuated position, the edge 313 of the cover 302 actuates the sensor 314; the sensor 314 is configured to be opened/closed when the cover 302 is put into the actuated state or moved away from it.

Figure 13:
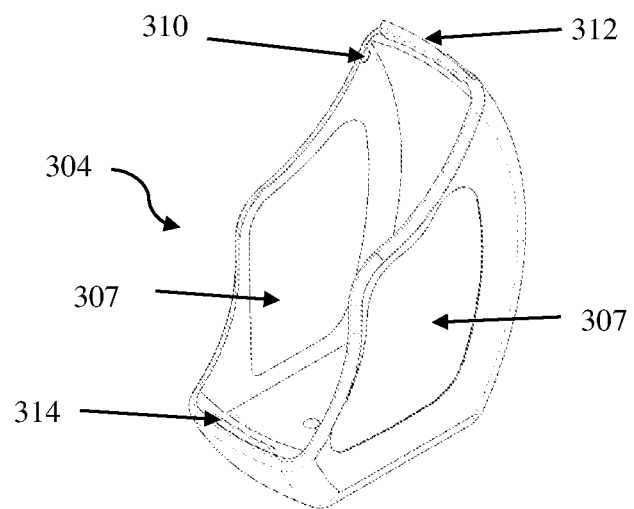
FIG. 13 is a perspective view of the adherence monitor shown in FIG. 12.
Figure 14:
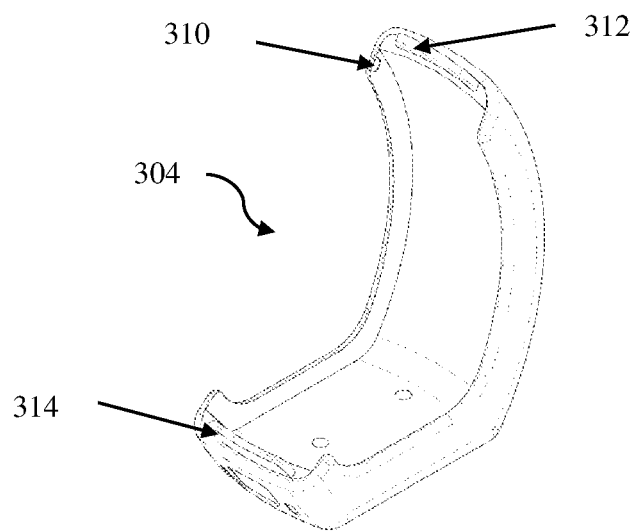
FIG. 14 is a perspective view of another possible embodiment of the adherence monitor.
Figure 15A:
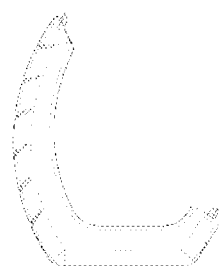
FIG. 15 A is the front view of another possible embodiment of the adherence monitor.
FIGS. 15B and 15C are the right and left views of the adherence monitor of FIG. 15A, respectively.
Figure 15B:
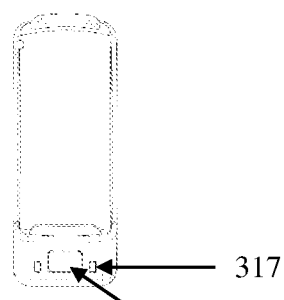
Figure 15C:
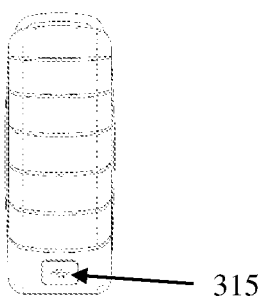

FIG. 13 shows a perspective view of the embodiment of the invention of FIG. 12. The adherence monitor 304 further includes a sensor (not shown) for detecting inhaler in/out. The sensor 315 may be a mechanical, electromechanical or electronic sensor. The sensor may be an optical IR sensor that detects the presence or absence of the base or wall of the inhaler within a certain distance by generating data output based on optical signal received.

In the embodiment illustrated in FIG. 13 the sensor is an optical IR sensor that detects the presence of absence of the base or wall of the inhaler within certain distance by generating data output based on the optical signal received. The sensor includes an infra-red light emitter and infra-red light receiver positioned in such way that the optical signal emitted from the emitter is reflected of the base or the wall of the medicament inhaler and received by the receiver. The data output of the receiver is processed by the ECM to determine if the output is consistent with 'inhaler in' or inhaler out' parameters recorded in the memory database.

The medicament inhaler may preferably include a retractable cover which is movable in relation to the inhaler housing and coupled to the dispensing mechanism such that when the cover is moved from an "at rest" position, through a primed position, and then to an actuated position, an audible click sound is generated and the medicament is ready for inhalation by the patient.

The cover removal sensor(s) may, in other implementations, be one or more mechanical, electromechanical or electronic switches. In another embodiment, the at least one switch may be optical, whereby a beam of light (e.g., IR light) may detect the presence of the cover when it is on the mouthpiece and the absence of the cover when the cover is removed from the mouthpiece.

In another embodiment, the cover removal sensor(s) may be mechanical detector switches. In such an embodiment, and for example, the cover may actuate and deactuate the switch(es) by physically engaging with and disengaging with the switch(es) respectively. Alternatively the cover may actuate and deactuate the switch(es) by changes in proximity to the switch(es). Any suitable device which can sense the movement of the cover may be used.

In one embodiment of the present invention, the adherence monitor housing is further adapted to grip the base of the inhaler and at least a portion of a wall opposite to the wall onto which the movable cover opens into the actuated position.

In another embodiment of the present invention, the adherence monitor housing is further adapted to have sufficient proximity to the cover to detect when the cover is in the "at rest" position and in the actuated position, and is further adapted to have no contact with the cover when it is between the "at rest" and the actuated position.

Further, the adherence monitor 304 includes an acoustic sensor (not shown) integrated into housing 305. The acoustic detection of actuation and/or inhalation is used in addition to the mechanical switch triggers to determine medication delivery events (both medication dispensing and inhalation). Preferably the acoustic sensor is placed in or near the base of the housing 305, but this location is intended as an illustration only and is not intended to be limiting. The acoustic sensor may be located in any suitable position within the housing 305. The acoustic sensor is not in direct contact with the inhalation pathway or medication flow, but held within the housing 305 to ensure that there is no interference with the flow of the medication into the patient's airways.

Figure 17:
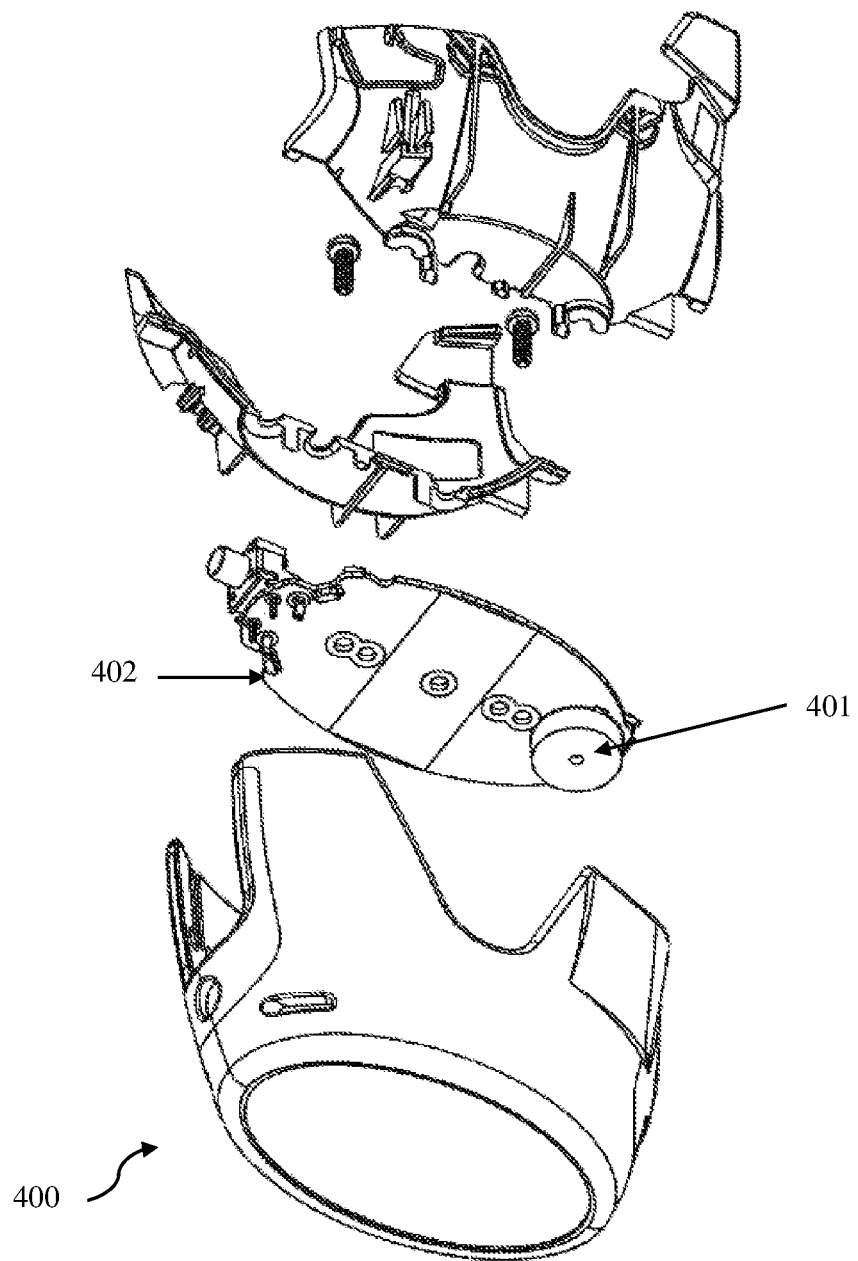
FIG. 17 is an exploded perspective bottom up view of the adherence monitor shown in FIGS. 5-8.

Referring to FIG. 17, one possible location of an acoustic sensor 401 is shown on the PCB 402 included in the adherence monitor 400.

Preferably, the acoustic sensor consists of a circuit that includes one or more microphones, an amplifier and a filter. In one example of the invention, the microphone may be an acoustic microphone, characterised by a small form, surface mount fit and low power consumption and analog output (Knowles Acoustics SPU0410HR5H-PB micro-electro-mechanical system (MEMS)). Alternatively and/or additionally, the microphone may have an analog output or digital output. In other embodiments the acoustic sensor may use multiple sensors. Analog filtering and a low power dual operational amplifier may be used to amplify the signal. A two stage gain control may be configured to control gain for the amplifier. The output of the microphone is coupled into the ECM via an ADC input. The microphone and amplifier may be powered via a ECM GPIO pin, allowing it to be powered up briefly when medication loading/actuation is detected, and powered down at all other times to maintain adherence monitor battery life.

The acoustic sensors are configured to generate output signals at prescribed times. This may include generating signals intermittently, periodically (e.g. at a sampling rate), continuously, continually, at varying intervals, or otherwise. The sampling rate may be at, for example, 5 ms or any suitable smaller or greater sampling rate.

Based on the testing of various inhalers we found a noticeable frequency peak around 13-15 kHz for both medication dispensing and inhalation. Preferably the signal is not processed at the frequency, but using the signal power envelope. For that purpose the signal is rectified to remove the DC offset and smoothed. It is noted that according to this implementation it is not required to provide a detailed frequency spectrum or analysis. A relatively simple implementation, in which a high pass filter or similar arrangement allows for the power levels at the targeted frequencies to be measured, is all that is required. This allows for an inhalation event to be identified as an increase in signal relative to the background level.

The ECM is programmed to sample the ADC output (bits) at a chosen sampling rate and to measure the signal energy. Positive actuation result and positive inhalation result is triggered by the algorithm when the signal exceeds a level threshold for a time threshold. This ensures that the positive result cannot be triggered by an intense burst of signal for a short time period that is too short to be a valid actuation or inhalation.

It will be appreciated that any suitable acoustic sensor, adapted to adequately detect the required frequency range and provide a corresponding output, could be used, for example suitable piezoelectric devices or other forms of acoustic sensors.

FIGS. 14 and 15A-C illustrate further possible embodiments of the adherence monitor 304. The adherence monitor 304 also includes a battery and memory (not shown), both included within one of the side walls or the base of the housing 305.

Preferably, the battery, the memory and the ECM are included within the base of the housing 305.

In another aspect of the present invention, the adherence monitor 304 includes a wireless communication means in communication with the ECM and memory, configured to send data to and/or receive data from remote locations and/or electronic devices external to the adherence monitor 304. In one embodiment, this may be in the form of, or provided for, by a USB port 315 located on the second housing 304. Alternatively and/or additionally, the adherence monitor 304 may be provided with a wireless transmitter and/or a wireless transceiver to be able to transmit and/or receive data respectively, for example a Bluetooth device or other suitable wireless communication arrangement.

The user interface may also be used to access any data received (or transmitted) by the adherence monitor or to control the upload of the data from the adherence monitor to an electronic device external to the adherence monitor or the medicament inhaler.

In one embodiment, this may be in the form of a multi-function status button 316 and LEDs 317 for monitoring several aspects of the adherence monitor 304. For example, pushing the button 316 once may result in a green LED showing if the adherence monitor 304 is fitted to the inhaler 301 correctly, and in normal working order. Conversely, a red LED may indicate a problem. Pushing the status button 316 twice may provide for another aspect of the adherence monitor to be checked or reported, and furthermore pushing and holding the status button 316 may result in yet another function or check being performed.

The adherence monitor 304 is adapted through its hardware, firmware and software to monitor, manipulate, store and transmit adherence data relating to the patient usage of the inhaler 301.

Having regard to FIG. 16 there is shown a flow chart illustrating one example of processing steps performed by the adherence monitor of FIG. 11 to determine if a valid medication inhalation has occurred.

First, following a detection of a cover removal sensor status change the ECM processes data output from the inhaler in/out sensor to detect the presence of the medicament inhaler in the adherence monitor. When the inhaler 301 is inserted into the adherence monitor 304, the ECM detects "inhaler in" utilising the input from any known sensors (e.g. optical sensor, pressure sensor).

Once the presence of the inhaler 301 in the adherence monitor 304 is detected by the controller, the ECM processes data output from the cover removal sensor 312 to detect the position of the cover 302. Following the cover change state signal (cover is open, when it has been closed previously), the ECM generates a time stamp for the event and stores 'COVER OPEN' event log.

On detection of movement of the inhaler cover 302 from the at rest position, the ECM triggers acoustic sensor to commence the first recording. It will be appreciated that there is an ongoing need to minimise power consumption in monitors for inhalers. In this implementation the acoustic sensor is only powered up when the cover is opened, as no valid inhalation event can occur until the cover is open.

At the next step, the ECM processes data output from the acoustic sensor. The output is compared to the reference parameters in the adherence monitor memory, to identify the presence or absence of the acoustic signature characteristic of the click sound generated by the cover in the actuated position.

At next step, ECM determines if the acoustic signature characteristic of the click sound was detected within a predetermined time from the time of the cover being moved from the at rest position.

At the following step, the ECM processes data output from the cover removal sensor to identify cover is in the actuated position.

At the next step, the ECM triggers the acoustic sensor to commence the second recording to detect inhalation signal. The ECM processes data output from the acoustic sensor and compares it to reference parameters in the memory to identify the presence or absence of the acoustic signature characteristic of inhalation of the medicament by the patient. If the ECM detects inhalation it generates a time stamp for the event and stores 'Inhalation' event log. The ECM may also determine if the acoustic signature characteristic of the inhalation of the medicament by the patient was detected within a predetermined time from the time of the cover being moved into the actuated position.

The precise nature of the acoustic signals detected will depend upon the construction of the inhaler, its intended usage, and the nature of the sensor and processing used. It may detect acoustic signals associated with inhalation by the user. It may detect sounds generated by the inhaler and characteristic of medicament dispensing, or preparations for such dispensing, for example clicks and other sounds generated by manipulation of the device. It may detect sounds associated with the release of a dose, for example the operation of a pMDI. Any suitable acoustic signal, which serves to indicate device or user activity, may be used. It will be appreciated that the frequency band of interest may change depending upon the signal selected. Further, it may be that some acoustic signatures may require a more sophisticated level of processing and analysis that that described above, which can be relatively simply implemented using a high pass filter.

It will be appreciated that the use of cover (or cap) position sensing, coupled with a separate acoustic sensor output, provides two factor verification that a dose of medicament has been dispensed. This use of independent sensors greatly reduces the risk of incorrect detection of a dose dispensing event, compared to either one alone. It allows for increased accuracy, as the chance of some event which is not dose dispensing and triggers both sensors is small. The sensors selected are relatively simple and inexpensive to implement, compared to multi-sensor alternatives.

Thus, the ECM is programmed to correlate inhaler in/out data, cover removal data and acoustic data to determine if a medication delivery event has occurred.

Once the ECM generates 'medication failed/no inhalation' logs or 'medication/inhalation' log, the ECM transmits any collected data to a remote computing device.

In some embodiments, the adherence monitor 304 described in the present invention may include a firmware for determining a cap-off event which is likely to constitute a medicament dose delivery event and distinguishing it from other cap-off events, e.g., as illustrated in FIG. 4.

Adherence monitors as described above include an ECM, with the ECM being adapted to monitor and/or manipulate and/or store and/or transmit all adherence data gathered, relating to the patient usage of the medicament delivery device. The ECM may be a suitable microprocessor device.

Preferably the ECM is a suitable processor which operatively receives acoustic sensor data from the acoustic sensor and cap removal data from the cap removal sensor. Preferably, the ECM is programmed with analysis software.

The use of ECM's, in conjunction with adherence monitors for medicament delivery devices, are well known, and it is not intended therefore to describe them in any significant detail herein. For example, these systems are in general terms in commercial use in products available from the present applicant and related companies, as well as disclosed in the applicant's prior patent filings, for example those incorporated by reference herein. An example of an adherence monitor, used in conjunction with an ECM and/or transmitter can be found in our U.S. Pat. No. 8,424,517 and our US Patent Publication No. 2014/0000598.

The ECM is powered by a battery, and either a rechargeable or replaceable battery may be used. The ECM and/or the adherence monitor may be alternatively be powered by any suitable alternative means, for example a kinetic charger, or by solar power.

The ECM stores and transmits the adherence data gathered, so that analysis can determine if the user has used the inhaler correctly and/or incorrectly. The inhaler use logs generated in the adherence monitor are uploaded into smartphone application, a PC or a central communication hub, and through those into a web based server. In some embodiments, the inhaler use logs may also be uploaded from the adherence monitor directly into a web based server.

Adherence monitors described above include a memory. In some embodiments, a volatile type computer memory, including for example RAM, DRAM, SRAM, may be used. In such instances, the adherence monitor may continually transmit information to the computing device external to the adherence monitor or medicament delivery device. In other embodiments non-volatile memory formats may be used, including for example ROM, EEPROM, flash memory, ferroelectric RAM (F-RAM), optical and magnetic computer memory storage devices, and others. In this case data may be only transmitted on command, or in a periodic manner, for example when the monitor is connected to a network suitable for communication with the intended external device.

The adherence monitors described above may also include indication means, such as at least one LED to indicate an event and/or to alert the user if the ECM determines that the user has used the inhaler correctly and/or incorrectly. The indication means may be utilised to alert the user if they have attempted to dispense a dose of medicament with the cap still attached or if the cap is not fully off (in case of Ellipta® inhaler). Alternatively, the indication means may be used to alert if medication has not been dispensed within certain timeframe, e.g. every 12 h or 24 h.

The indication means may be in the form of one or more LEDs as illustrated, or in the form of some other visual and/or audio and/or vibrational indicator. Adherence monitors may also include a multi-function user button for monitoring and controlling several aspects of operation. For example, pushing the button once may result in a green light showing if the adherence monitor is fitted to the respective inhaler correctly, and in normal working order. Conversely, a red light may indicate a problem. Pushing the button twice may provide for another aspect of the adherence monitor to be checked or reported, and furthermore pushing and holding the button may result in yet another function or check being done.

The adherence monitors described herein may also include user interface enabling the user to access data recorded or received by the adherence monitor and also change the settings of the adherence monitor (for example, date/time, visual/audio alert settings). The user interface may also be used to access any data received (or transmitted) by the adherence monitor or to control the upload of the data from the adherence monitor to an external electronic device.

The user interface may include at least one operational button and/or an LCD screen and/or audio/visual notification means to notify or remind the patient of a particular event. The user interface may be configured to alert users of any usage errors. Such a user interface may alternatively be provided using an app or similar arrangement on a smartphone, tablet or similar device.

The embodiments of the adherence monitors and/or the ECM described herein may be able to monitor for any type of non-dose counting information relating to the operation of the inhaler, and/or patient usage of the inhaler. For example, the ECM may include a real time clock (or be in electronic communication with one) to enable the adherence monitor to record a date and time for each dose of medicament dispensed. The ECM may be calibrated to compare the actual doses dispensed against the table of pre-set dosage times and, if the dose is not dispensed at the pre-set time, alert the user that a dose is due.

Furthermore, and for example only, adherence monitors and/or the ECM described herein may also be able to monitor criteria such as geographical location, temperature, humidity, the orientation of the inhaler, the condition of the medicament, the amount of medicament left, the condition of the battery or whether it is installed, the flow or pressure of the user's inhalation, an audio sensor for detecting inhalation or for determining if the main body portion has been rotated with respect to the base portion, and so on. To this effect, the ECM may include an audio or optical inhalation sensor, thermistor sensor or accelerometer, or be connected to a GPS (e.g. the adherence data from the smartphone paired with the adherence monitor may be matched with the GPS data relating to the location of adherence events received by the smartphone).

The adherence monitors described herein may also include sensors detecting the orientation of the inhaler during the medication dose priming and/or inhalation. Such sensors are known in the art and include accelerometers, gyroscopic sensors or tilt switches.

Adherence monitors described herein also generally include a communication device for transmitting the adherence data. The communication device may be in electronic communications with the ECM and either a standalone component, or part of the ECM. In one embodiment, this may be a USB port located on the housing of the adherence monitor. Any other suitable wired connections or ports may be used.

Alternatively and/or additionally, the adherence monitors described herein and/or ECM may be provided with a wireless transmitter and/or a wireless transceiver e.g. Bluetooth Low Energy® module to be able to transmit and/or receive data respectively. Any other suitable wireless technology known in the art may be used, including for example Wi-Fi (IEEE 802.11), any suitable Bluetooth® technology, other radio frequencies, Infra-Red (IR), GSM, CDMA, GPRS, 3G, 4G, W-CDMA, EDGE or DCDMA200 or similar.

The data may be transmitted to a remote computer server or to an adjacent electronic device such as a smart phone or electronic tablet. The adherence monitor may be paired with a smartphone loaded with a software application which allows the smartphone to access, process, and/or present the data collected by the adherence monitor. The smartphone may be configured to transfer the data obtained from the adherence monitor to a web services platform. The data may be transmitted in real time, manually or at predetermined set times. For example, some of the processing functions described as undertaken by the monitor may instead be undertaken by the processor in a smartphone (or other device), and only raw or partly processed data may be sent from the monitor to the smartphone. For example, the cap removal and cap replacement data may be sent to the smartphone, which then determines from the time interval whether the log events are consistent with a dose dispensing event. All the processing steps described could be performed in suitable implementations by processors other than in the monitor, if desired.

The person receiving the adherence data may then be able to review the patient's use of the medicament inhaler and be alerted to any matters of interest or concern. For example, a health professional may be alerted if the user frequently leaves the cap off the mouthpiece of the medicament inhaler. The health professional may then contact the user to discuss these findings and perhaps offer advice on better use or care of the medicament inhaler.

In some embodiments, the ECM may also be configured to receive information from the remote location and/or electronic devices external to the adherence monitor using the communication means.

While the embodiments described above are currently preferred, it will be appreciated that a wide range of other variations might also be made within the general spirit and scope of the invention.

Preferably, the ECM may utilise the adherence data gathered to determine if the user has used the medicament delivery device correctly and/or incorrectly. This may be achieved by incorporating an appropriate algorithm(s) within the ECM or other user devices, for example a tablet or smartphone, or a remote system, to analyse the adherence data gathered and/or to draw an appropriate conclusion.

Further, the cap detection sensors of the present invention may be embedded directly in an electronically enabled medicament dispenser, rendering the use of separate adherence monitor unnecessary. It will be appreciated that the cap detection sensors would need to be disposed within the housing of the inhaler, with provision for the processor, switch, etc. in the inhaler.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All patent and other references noted in the specification, including websites, are hereby incorporated by reference.

The invention claimed is:

1. A monitor for an inhaler, the inhaler including:
an inhaler housing having a cap attached to the inhaler housing via a tether or a hinge,
a mouthpiece configured to be removably covered by the cap, the cap configured to move between a cap on and a cap off position, and
a medicament chamber coupled to the mouthpiece, wherein the mouthpiece provides a dose of medicament to a user;
the monitor configured to releasably attach to the inhaler, the monitor including:
a monitor housing, releasably attachable to the inhaler, and comprising:
an inner shell and an outer shell;
at least one retention projection configured to assist in retaining the inhaler, wherein the at least one retention projection includes at least one retaining catch and wherein the at least one retention projection is spring-loaded; and
a cap detector configured to detect when the cap is covering and/or not covering the mouthpiece,
wherein a gap is provided between at least part of the inner shell and the outer shell, such that at least a portion of the monitor housing is adapted to flex to receive the inhaler therein.

2. The monitor according to claim 1, wherein the at least one retention projection is configured to flex to facilitate insertion and removal of inhaler.

3. The monitor according to claim 1, wherein the at least one retention projection is formed of flexible plastic or metal.

4. The monitor according to claim 1, wherein the cap detector is a switch configured to be deactivated and/or activated by the opening and/or closing of the cap of the inhaler in use.

5. The monitor according to claim 4, wherein the switch is spring loaded.

6. The monitor according to claim 1, further comprising a proximity sensor adapted to detect the absence and/or presence of the inhaler within the monitor housing.

7. The monitor according to claim 1, further comprising at least one sensor including an audio sensor, an optical inhalation sensor, a thermistor, and an accelerometer.

8. The monitor according to claim 1, wherein the inhaler further includes a perforation mechanism.

9. The monitor according to claim 1, further comprising an electronic control module including a processor, wherein the processor is configured to operatively receive cap on data and cap off data from the cap detector, the processor configured to determine that a dose of medicament has been dispensed only if the cap on data and the cap off data indicates that the cap has been removed and replaced, and that a predetermined minimum time period has elapsed between cap removal and cap replacement.

10. The monitor according to claim 9, wherein the processor is further configured to determine that a dose of medicament has been dispensed only if the time between cap removal and cap replacement is further less than a predetermined maximum time.

11. The monitor according to claim 9, further comprising an acoustic sensor configured to detect one or more of an inhalation event, a medication dispensing event, a medication preparation step, or an inhaler activation step.

12. The monitor according to claim 11, wherein the processor is further configured to operatively receive acoustic sensor data from the acoustic sensor and determine that a dose of medicament has been dispensed when the acoustic sensor data indicates that an acoustic signal consistent with the dispensing of medicament has occurred after the cap has been removed and before the cap has been replaced.

13. A monitor for an inhaler, the inhaler including:
an inhaler housing having a cap attached to the inhaler housing via a hinge,
a mouthpiece configured to be removably covered by the cap, the cap configured to move between a cap on and a cap off position, and
a medicament chamber coupled to the mouthpiece, wherein the mouthpiece provides a dose of medicament to a user;
the monitor configured to releasably attach to the inhaler, the monitor including:
a monitor housing, releasably attachable to the inhaler, and comprising:
an inner shell and an outer shell;
at least one retention projection configured to assist in retaining the inhaler, wherein the at least one retention projection includes at least one retaining catch; and
a cap detector configured to detect when the cap is covering and/or not covering the mouthpiece,
wherein a gap is provided between at least part of the inner shell and the outer shell, such that at least a portion of the monitor housing is adapted to flex to receive the inhaler therein and
wherein the at least one retention projection comprises two retention projections arranged on opposing sides of the monitor housing and configured to be positioned adjacent the hinge of the cap of the inhale when the inhaler is inserted into the monitor housing.

14. A system configured to monitor delivery of a dose of medicament by an inhaler, the system including:
an inhaler; and
the monitor of claim 1.

* * * * *